United States Patent
Shaquer (10) Patent No.: US 7,171,273 B2
(45) Date of Patent: *Jan. 30, 2007

(54) TRANSCUTANEOUS POWER OPTIMIZATION CIRCUIT FOR A MEDICAL IMPLANT

(75) Inventor: Cem M. Shaquer, Russell Lea (AU)

(73) Assignee: Cochlear Limited, Lane Cove (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/883,809

(22) Filed: Jul. 6, 2004

(65) Prior Publication Data

US 2005/0131491 A1    Jun. 16, 2005

Related U.S. Application Data

(62) Division of application No. 09/654,731, filed on Sep. 5, 2000, now Pat. No. 6,810,289.

(30) Foreign Application Priority Data

Apr. 20, 2000    (WO) .................... PCT/AU00/00371

(51) Int. Cl.
   *A61N 1/18* (2006.01)
(52) U.S. Cl. ........................................ 607/57
(58) Field of Classification Search .......... 607/57, 607/63, 61
   See application file for complete search history.

(56) References Cited

U.S. PATENT DOCUMENTS

| 4,357,497 A | 11/1982 | Hochmair et al. |
| 4,918,745 A | 4/1990 | Hutchison |
| 5,042,084 A | 8/1991 | Daly |
| 5,584,870 A | 12/1996 | Single et al. |
| 5,603,726 A | 2/1997 | Schulman et al. |
| 5,755,748 A * | 5/1998 | Borza ...................... 607/61 |
| 5,876,425 A * | 3/1999 | Gord et al. ................ 607/56 |
| 6,002,966 A | 12/1999 | Loeb et al. |
| 6,227,204 B1 | 5/2001 | Baumann et al. |
| 6,301,505 B1 * | 10/2001 | Money .................... 607/63 |
| 6,570,363 B2 | 5/2003 | Boberschmidt et al. |

(Continued)

FOREIGN PATENT DOCUMENTS

CA    2227090    7/1999

(Continued)

OTHER PUBLICATIONS

Zierhofer, et al., "Electronic Design of a Cochlear Implant for Multichannel High-rate Pulsatile Stimulation Strategies," IEEE Transaction on Rehabilitation Engineering, vol. 3, No. 1, Mar. 1, 1995.

(Continued)

*Primary Examiner*—Jeffrey R. Jastrzab
(74) *Attorney, Agent, or Firm*—Jagtiani + Guttag (57) ABSTRACT

In a cochlear implant system, the implantable stimulator includes a monitor which monitors parameters associated with the stimulation signals and/or the power stored in an energy storage element which stores energy transmitted from the processor. This parameter or parameters is/are analyzed and one or more feedback signals are generated and transmitted back to the processor. The processor uses the feedback signal to insure that power is transmitted to the stimulator optimally and that the stimulation signals are compliant.

19 Claims, 4 Drawing Sheets

U.S. PATENT DOCUMENTS 6,671,552 B2    12/2003    Merritt et al.
6,810,289 B1 *  10/2004    Shaquer ........................ 607/57

FOREIGN PATENT DOCUMENTS

WO          WO99/44684          9/1999

OTHER PUBLICATIONS

European Supplementary Search Report, Ep 00 91 8608, Feb. 5, 2004.
International Search Report for PCT/AU00/00371, Jun. 13, 2000.
International Search Report for PCT/AU04/24163, Feb. 18, 2005.

* cited by examiner

Fig 4b.   $V_{DD} \cong V_T$

TRANSCUTANEOUS POWER OPTIMIZATION CIRCUIT FOR A MEDICAL IMPLANT

CROSS-REFERENCE TO RELATED APPLICATIONS

This application is a divisional of U.S. application Ser. No. 09/654,731, entitled "Transcutaneous Power Optimization Circuit for Cochlear Implant," filed on Sep. 5, 2000, now U.S. Pat. No. 6,810,289, which claims the priority of PCT/AU00/00371, entitled "Transcutaneous Power Optimization Circuit for Cochlear Implant" filed on Apr. 20, 2000. The entire disclosure and contents of the above patents and applications are hereby incorporated by reference.

BACKGROUND OF THE INVENTION

A. Field of Invention

This invention pertains to an optimization circuit in a cochlear implant system and more particularly to a circuit which monitors one or more parameters within the implant such as the internal power supply level and the compliance of the stimulation signals applied by the implant. If an undesirable condition is indicated by these parameters, the circuit generates control signals to correct the condition by adjusting the coupling between the internal and external components of the system.

B. Description of the Prior Art

Certain patients suffer from a hearing disability in the inner ear which cannot be satisfactorily assisted by normal hearing aids. However, if the aural nerve is intact, the patient may have some aural functions restored with a cochlear implant system. A typical cochlear implant system presently available includes an external component or processor and an internal component often called the implanted stimulator. The external component includes a microphone for receiving ambient sounds and converting them into electrical signals, a processor for processing said electrical signals into encoded signals and a transmitter transmitting said encoded signals to the internal component.

The internal component includes a receiver receiving the encoded signals, a decoder for decoding said signals into stimulation signals and an electrode array including both intracochlear electrodes extending into the patient's cochlear and optionally one or more extra-cochlear electrodes. The stimulation signals are applied in the form of pulses having durations and waveshapes determined by the processor.

Because the internal component of the cochlear implant system is relatively small, it is not normally provided with its own permanent power supply. Instead, the internal component is energized transcutaneously by RF signals received from the external component with the use of two inductively coupled coils, one provided in the external component and the other being provided within the internal component. The external component sends data to the internal component, by first encoding the data into the RF signals and then transmitting it across the transcutaneous link. The internal component decodes the data from the received RF signals and also stores the received RF energy in a capacitor to power its electronics. In order to achieve efficient power transfer across the transcutaneous link, both coils are tuned to resonate, at or close to the operating frequency of the transmitter and are held in axial alignment with the aid of a magnetic coupling.

The amount of energy being transferred to the internal component depends mainly on the amount of inductive coupling between the two coils as well as the resonance frequency of the respective coils. The former is dependent on the thickness of the tissue separating the two coils, which thickness varies over the patient population. Hence, for identical cochlear implant systems the efficiency of energy transfer varies from one patient to another.

The required amount of energy varies with the patient, (due to the electrode-tissue interface impedance being patient specific) the system programming, and the sound environment. Therefore, every cochlear implant system must be designed so that adequate power is delivered to the internal component for all patients under all conditions. Hence, there is an excess energy transfer across the link for patients with relatively smaller separation between the coils, or a low electrode-tissue interface impedance, resulting in a shorter battery life, than optimally desired.

Attempts have been made by others to resolve this problem but they have not been entirely satisfactory. For example, U.S. Pat. No. 5,603,726 discloses a multichannel cochlear implant system in which the implantable section generates signals to a wearable processor indicative of the status of the implantable section, such as its power level and stimulation voltages. The information is used by the wearable processor to modify the characteristics of the signals transmitted. More particularly, the implantable section has an internal power supply capable of producing several outputs having different nominal DC levels. Additionally, the implantable section is also capable of providing unipolar or bipolar stimulation pulses between various intercochlear electrodes as well as an indifferent electrode. A telemetry transmitter is used to send data to the wearable processor, the data being indicative of the voltage levels of the power supply outputs, the amplitudes of the stimulation signals and other parameters. The wearable processor uses the power level signals to adjust the amplitude (and therefore the power) of the RF signals transmitted to the implantable section. However, this approach is disadvantageous because it requires an RF transmitter having a variable programmable amplitude, and utilizes a fixed tuning of the transmit coil, therefore making no attempt to modulate the voltage on the tank capacitors to track the voltage required to maintain system compliance. Obviously such a transmitter is expensive to make and more complex then a standard RF transmitter having a preset amplitude. Moreover, sending information from the implantable section about the amplitude of the stimulation pulses after these pulses have already been applied is ineffective because, if one of these pulses is out of compliance, the external section can do nothing about it, except crank up the power to insure that future pulses are compliant. However, merely cranking the power without any further intelligence wastes energy.

Commonly assigned application Ser. No. 09/244,345 filed Feb. 4, 1999 entitled HIGH COMPLIANCE OUTPUT STAGE FOR A TISSUE STIMULATOR, incorporated herein by reference, describes a cochlear implant system wherein the generation of stimulation pulses is monitored, (i.e. the compliance of the stimulation generation circuit) and a voltage multiplier is used if necessary to ensure that the stimulation pulses are of the desired intensity. This application essentially deals with a system of improving the internal power supply in order to eliminate stimulation pulses, and as such, there is no provision in this application for transmission of data back to the external section.

OBJECTIVES AND SUMMARY OF THE INVENTION

In view of the above disadvantages of the prior art, it is an objective of the present invention to provide a power control circuit for a cochlear implant which is constructed and arranged to automatically and dynamically optimize the power transferred to the internal component based on one or more preselected criteria by adjusting an inductive coupling therebetween.

A further objective is to provide a power control circuit for a cochlear implant which is constructed and arranged to automatically and dynamically regulate the inductive coupling with the internal component thereof to insure that power is not wasted, thereby increasing the life of the external component battery.

A further objective is to provide a cochlear implant system wherein the external and internal systems are coupled inductively, wherein the voltage of the internal supply is monitored and the frequency of this coupling is tuned to obtain optimal power transfer using the voltage as a feedback signal.

Yet another objective is to provide a cochlear implant system wherein the compliance of the stimulation signals is monitored and used as a feedback signal to optimize the power transfer to the internal component.

Yet a further objective is to provide a cochlear implant with a compliance monitor arranged and constructed to sense a possible out of compliance condition before the respective stimulation pulse is completed and to adjust the power transferred to the internal section in such a manner that the out of compliance condition is averted.

Other objectives and advantages of the invention shall become apparent from the following description.

Briefly, a cochlear implant system constructed in accordance with this invention includes an external speech processor and an implantable stimulator having electronic circuitry, the two components being coupled to each other inductively by respective coils. Each coil is part of a tank circuit. The external speech processor transmits RF signals through the coupling. The implantable stimulator uses these signals for two purposes. First, the energy of the signals is stored in a storage element such as a capacitor and used to power the electronic circuitry. Second, the signals are decoded and used to derive the stimulation signals applied to the aural nerve.

In one embodiment of the invention, a parameter indicative of the voltage of the storage element is monitored and sent back to the speech processor via a secondary channel. The external speech processor then adjusts the frequency of its tank circuit to regulate the power transferred to the internal component to optimize it.

Additionally, or alternatively, the compliance of the stimulation signals is monitored and used as a feedback signal to control the frequency of the tank circuit to optimize power transfer to the internal component. This adjustment can be done either based on statistical basis, or in response to an individual and specific out of compliance condition.

DETAILED DESCRIPTION OF THE INVENTION

Figure 1:
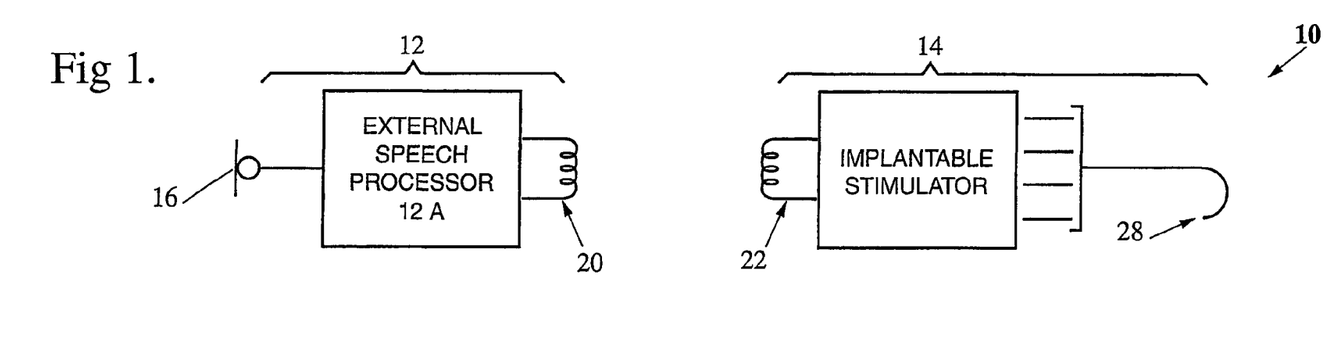
FIG. 1 shows a schematic diagram of a cochlear system constructed in accordance with the present invention.

Referring first to FIG. 1, a cochlear implant system 10 constructed in accordance with this invention includes an external component 12 and an internal component 14. The external component includes a speech processor 12A and is associated with a microphone 16 for sensing ambient sounds and generating corresponding electrical signals. These signals are sent to the speech processor 12A which processes the signals and generates corresponding encoded signals. The encoded signals are provided to a transmitter (including a transmit coil 20) for transmission to the internal component 14.

The internal component 14 (which may also be referred to as an implantable stimulator) receives the power and data via a receive coil 22. The RF power signal is stored by a power supply 24 (See FIG. 3) which provides power for the internal component 14. The data signals control the operation of the internal component 14 so as to generate the required stimulation pulses which are applied to the auditory nerve of the patient via an electrode array 28.

Figure 2:
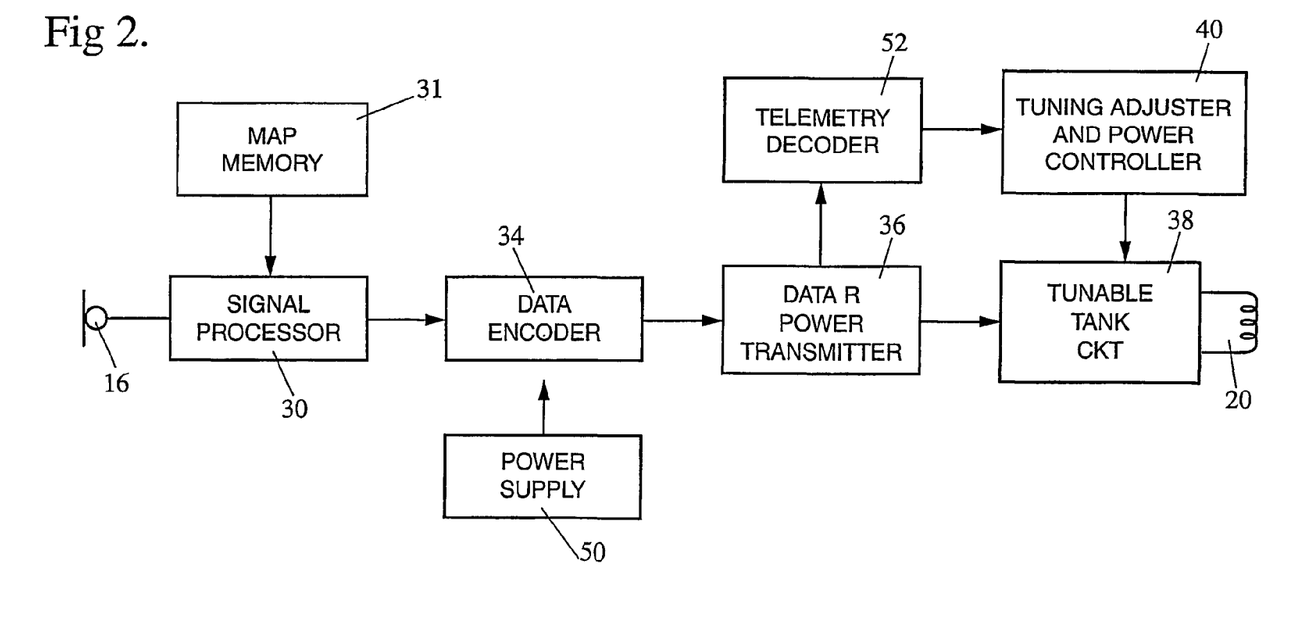
FIG. 2 shows a schematic diagram of the external component of the cochlear system of FIG. 1.

The structure of the external speech processor 12A is shown in more detail in FIG. 2. First, the audio signals received from microphone 16 are fed to a signal processor 30. This signal processor 30 maps the audio signals into excitation signals in accordance with one or more mapping algorithms stored in a map memory 31. These excitation signals are encoded by a digital data encoder 34. The encoder data is combined with an RF signal in the data and power transmitter 36, and passed to the transmit coil 20 via a tuneable tank circuit 38.

In accordance with the present invention, encoded telemetry data is received back from the internal component 14 via coil 20, and is decoded by telemetry decoder 52. The decoder telemetry data is passed to the tuning adjuster and power controller 40, which uses the telemetry data to generate a tuning adjustment signal. The tuneable tank circuit 38 adjusts the tuning of the transmit coil 20 according to the tuning adjustment signal as described in more detail below. This can be achieved, for example, by using an electrically controlled variable capacitor in conjunction with a series tuning capacitor, or by any of various similar means known to the art. Power to the whole system 10 is provided by a power supply 50 which typically includes a battery.

Figure 3:
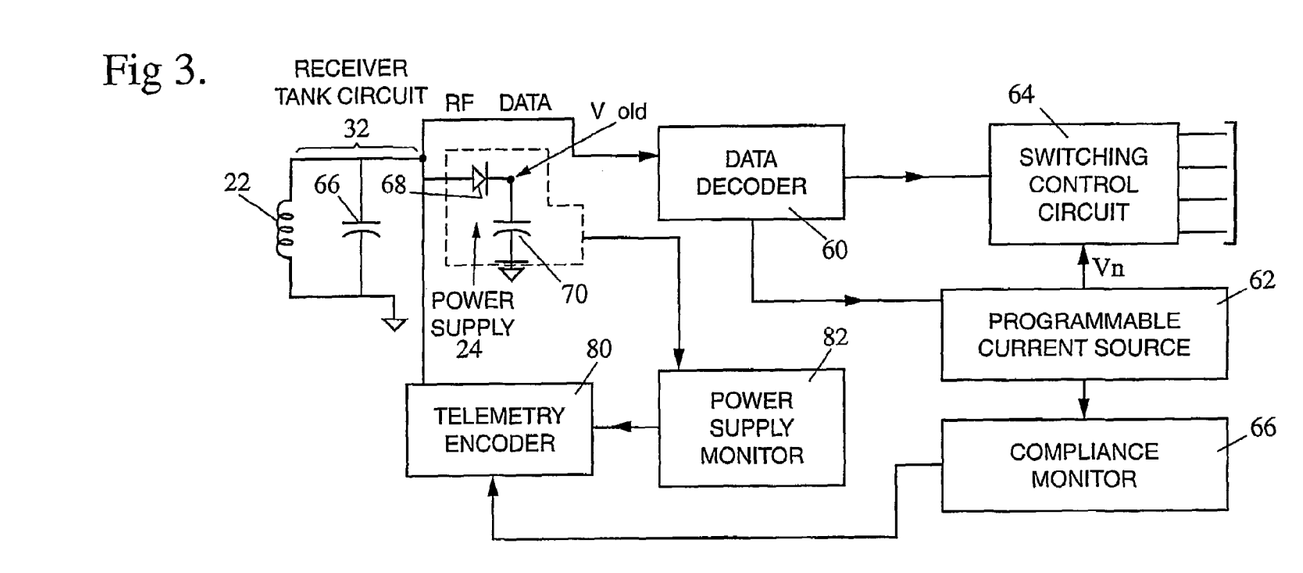
FIG. 3 shows a schematic diagram of the internal component of the cochlear system of FIG. 1.

Referring now to FIG. 3, the internal component 14 includes a housing (not shown) which is hermetically sealed. The component 14 also includes a receiver tank circuit 32 having the receive coil 22 and a capacitor 66. Signals received through this tank circuit are fed to a power supply 24 generating an output voltage Vdd. The power supply is represented in FIG. 3 by a diode 68 charging a capacitor 70.

The power supply 24 uses the energy of the received RF signals to charge up the capacitor 70.

The RF signals are also fed to a data decoder 60. The data decoder 60 derives from the RF signal the digital excitation signals generated by the data encoder 34 and generates corresponding stimulation control signals. These signals are fed to a programmable current source 62 and a switching control circuit 64. These two circuits cooperate in response to the signals from data decoder 60 to apply the cochlear stimulation signals to predetermined electrodes of electrode array 28 in a known manner which is beyond the scope of this invention.

Implant 14 further includes a compliance monitor 66 which generates an output that is fed to a telemetry encoder 80 as discussed more fully below; and a power supply monitor 82 which is used to monitor the voltage Vdd generated by power supply 24 and which provides a voltage condition signal to telemetry encoder 80.

The compliance monitor 66 and power supply monitor 82 each sense certain specific functions of the internal component and transmit them to the telemetry encoder 80. The telemetry encoder 80 then transmits this information to the telemetry decoder 52. The data is decoded and used to adjust the power transmit between the coils, if necessary.

Figures 4A, 4B, 4C:
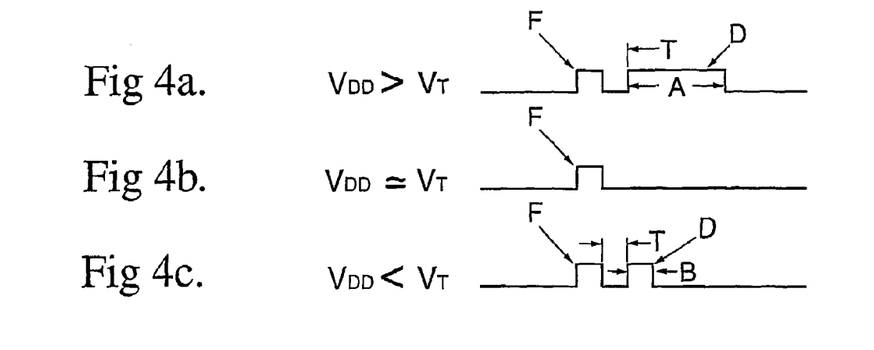
FIGS. 4A, 4B and 4C show the power control signals transmitted from the internal to the external components respectively to indicate the power level induced within the internal component.

An exemplary mode of operation indicating the voltage monitoring made is now described in conjunction with FIGS. 4A, B and C and 5A and 5B. At predetermined intervals, for example, every 100 ms, or alternatively after every stimulation pulse, the telemetry encoder 80 generates a first pulse F. (Step 100). This pulse may have a duration of about 1 ms. This pulse F indicates to the external speech processor 12A that the implantable stimulator 14 is sending data.

Figure 5A:
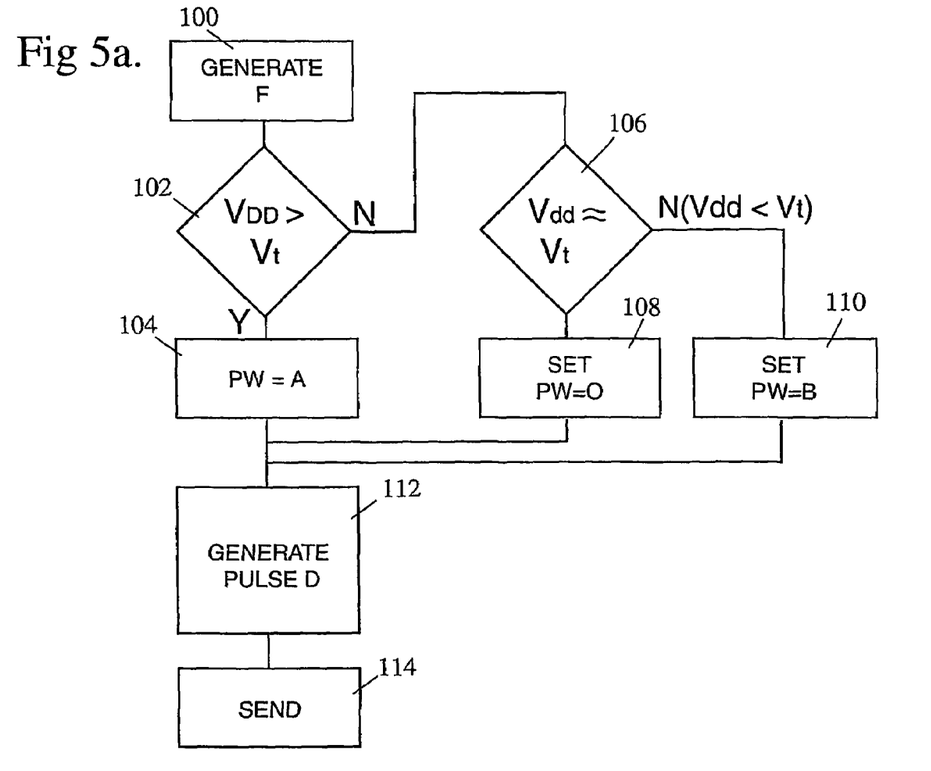
FIGS. 5A and 5B show flow charts for the operation of internal and external components of FIGS. 1–3, respectively.

Next, the power supply monitor 82 compares the power supply output voltage Vdd to a threshold value Vt and sends the result to the telemetry encoder 80. More specifically, starting with step 102, the power supply monitor 82 first determines if Vdd>Vt. If it is, then in step 104, a parameter pw (pulse width) is set to a predetermined value A, of for example, 2 ms by the telemetry encoder 80.

If in step 102 Vdd is not larger than Vt then in step 106 a check is performed to determine if Vdd is approximately equal to Vt. If it is, then in step 108 parameter pw is set to zero. If it is not then, Vdd must be smaller than Vt and in step 110 the parameter pw is set to a predetermined value B of, for example, 1 ms.

Next, in step 112 a pulse D is generated having a pulse width A or B, or no pulse is generated, depending on the outcome of the decisions 102 and 106. The pulse D (if present) is generated a period T after pulse F. T may be about 1 ms. The results of this step are seen in FIGS. 4A, 4B, 4C.

For FIG. 4A it has been determined that Vdd>Vt, and hence pulse D with a pulse width A is sent about 1 ms after pulse F.

In FIG. 4B, Vdd has been found to be about equal to Vt and hence no pulse D is present.

In FIG. 4C, Vdd is found to be smaller that Vt and hence pulse D having a pulse width B is sent about 1 ms after period F, pulse width B being generally shorter than pulse width A. For example, pulse width A may be 2 ms and pulse width B may be about 1 ms.

Pulse F and, if present, pulse D are then sent to the tank circuit 32. As a result, a corresponding signal appears on the transmit coil 20, which is then decoded by the telemetry decoder 52.

Figure 5B:
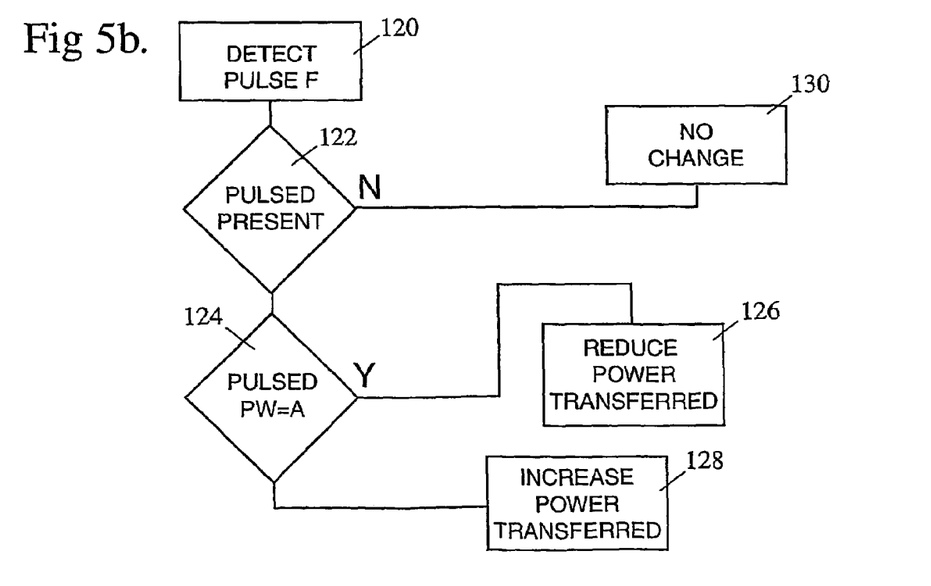

The operation of the telemetry decoder 52 is now described in conjunction with FIG. 5B. Starting with step 120, a pulse F is first detected which indicates that the power supply monitor 82 is sending information about the status of the power supply 24. Next in step 122 a check is made to determine if a pulse D is present following pulse F. If this pulse is not detected, then in step 130 the previous operations are continued with no change.

If in step 122, a pulse D is detected then in step 124 a determination is made as to whether this pulse D has a pulse width A or a pulse width B. A telemetry pulse D having a relatively long pulse width, in a range corresponding to the pulse width A (for example if pulse D exceeds 1.5 ms), indicates that the implant supply voltage is high (i.e. Vdd>Vt). In step 126, the tuning adjuster and power controller 40 therefore adjusts the tunable tank circuit 38 to reduce the power transferred to the implant. A preferred method to accomplish this effect is to reduce the resonance frequency of the tank circuit.

If the telemetry pulse is less than 1.5 ms, (indicating a pulse width B and that the power supply Vdd<Vt) then in step 128 the tuning adjuster and power controller 40 adjusts the tunable tank circuit 38 to increase the transferred power.

The tunable tank circuit 38 is adjusted by the tuning adjuster and power controller 40 via means of a tuning capacitor (not shown) which is preferably a voltage dependent capacitor. It should be appreciated that the tunable tank circuit 38 could also be tuned by other known means as would be understood by one skilled in the art.

Similarly, the above mentioned operation may be performed in respect of the compliance monitor signal, as described in more detail below.

Figure 6:
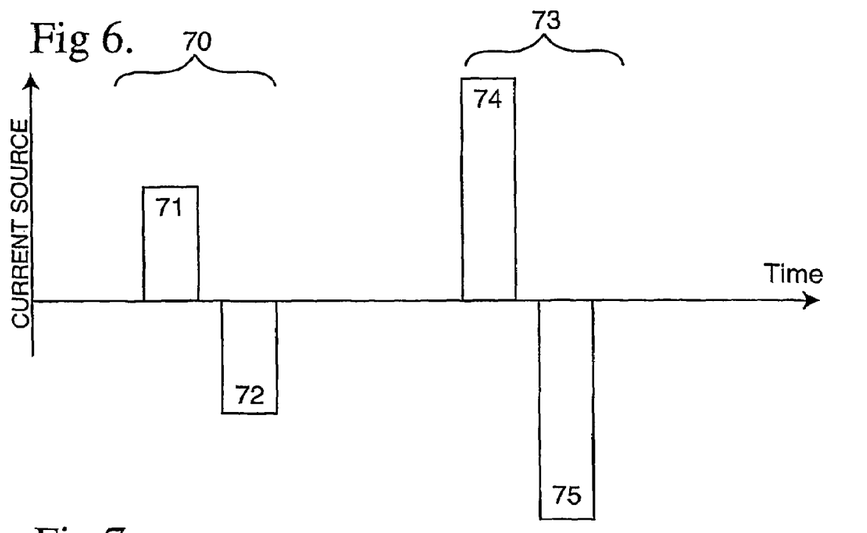
FIG. 6 shows two sets of typical biphasic stimulation signals defined by the speech processor.

Briefly, referring to FIG. 3, under the control of commands from data decoder 60, the programmable current source 62 generates current pulses which are applied to the electrodes by switching control circuit 64. FIG. 6 depicts two typical stimulation current waveforms 70 and 73 which may be requested by the signal processor 30. It can be seen that each waveform is biphasic, consisting of two current pulses of equal amplitude and opposite polarity. Thus, lower amplitude biphasic current waveform 70 consists of positive and negative pulses 71 and 72 respectively, and higher amplitude current waveform 73 consists of positive and negative pulses 74 and 75.

Figure 7:
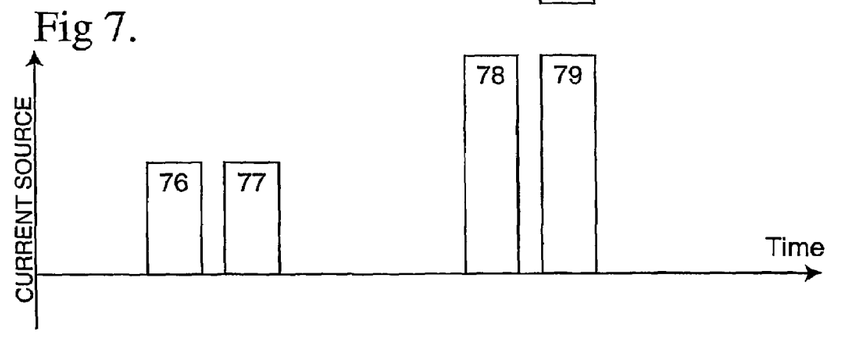
FIG. 7 shows the current pulses required to produce the stimulation pulses of FIG. 6.

Next, FIG. 7 depicts the corresponding current waveforms that must be generated by the programmable current source 62 to produce the desired stimulation current waveforms 70 and 73. That is, the programmable current source 62 must generate two lower amplitude square waves 76 and 77 to generate stimulus pulses 71 and 72 respectively, and two larger amplitude square waves 78 and 79 to generate the stimulus pulses 74 and 75. Pulses 77 and 79 are reversed by the switching control circuit 64. However, if the current pulses 78 and 79 exceed the capability of the power supply 24, an out of compliance condition occurs. This problem is resolved in the present invention as follows.

Figure 8:
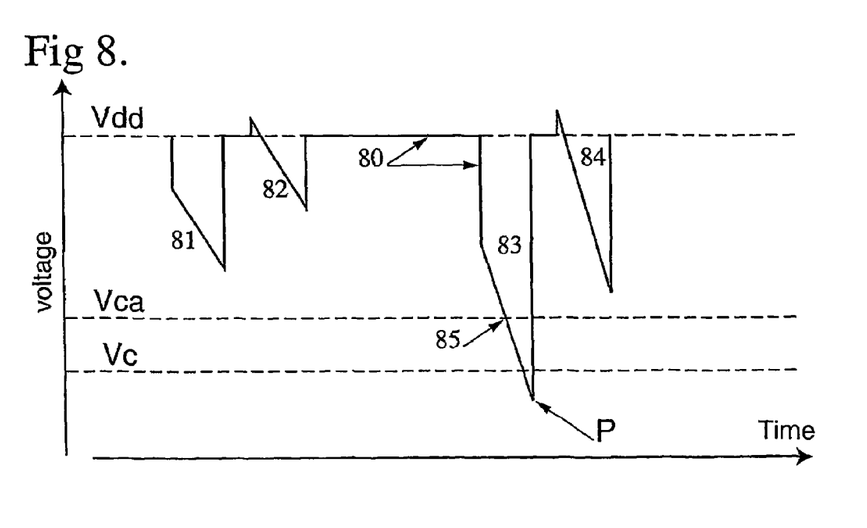
FIG. 8 shows the corresponding waveforms across the current source.

Referring to FIG. 8 the voltage waveform 80 represents the voltage Vn at the output of the programmable current source 62. It can be seen from the shape of the voltage waveform 80 that the load contains a capacitive component. The level Vc marks the minimum voltage across the programmable current source 62 at which compliance with the desired current waveforms of FIG. 7 can be maintained. The voltage Vca is a little higher than Vc as shown and is selected to provide a safety margin. As seen in FIG. 8, pulse 83 required to generate pulses 78 and 74 of FIGS. 7 and 6 respectively, starts off at a level above Vca but decreases linearly toward a minimum value (P) which is substantially below level Vc and therefore is not attainable. When this pulse reaches Vca (at point 85), the compliance monitor 66 generates a compliance monitor signal indicating an out of compliance condition. The signal is encoded by the telemetry encoder 80 and transmitted to the external processor. The signal may be the same signal as when VDD drops below VT as discussed above, or it may be a different signal, as would be appreciated by one skilled in the art. In response, the tuning adjuster and power controller commands the tunable tank circuit 38 to increase the voltage transmitted to the internal section.

The adjustment of the link tuning or RF power generated can be performed for every instance of a compliance monitor signal being received from the implant and may be maintained at a high level for a predetermined time, after which the RF power can be dropped to a previous level.

Alternatively, the frequency of the compliance monitor signal may be monitored by the tuning adjuster and power controller 40. The link tuning or RF power generated could then be adjusted to maintain a desired ratio of compliance monitor signals to stimulation signals. For example, the link tuning or RF power generated could be adjusted to keep the ratio of compliance monitor signals to stimulation pulses to a desired target of for example 5%, i.e. For this purpose, the tuning adjuster and power controller 40 includes a counter which counts every instance of non-compliance. After a predetermined number of stimulation pulses, for example a thousand, the counter is checked to determine the number of non-compliant instances. If the counter shows a number over the desired target (i.e. 50 for a 5% target) then the tuning adjuster and power controller 40 adjusts the tank circuit 38 to increase its power level. On the other hand for a number of non-compliant instances below the target, the power level is increased. Of course, this determination could also be made within the implant by the compliance monitor itself, as would be evident to one skilled in the art.

Obviously numerous modifications can be made to the invention without departing from its scope as defined in the appended claims.

I claim:

1. A cochlear implant system comprising:
    a processor configured to convert ambient sounds into stimulation signals;
    a transmitter configured to transmit said stimulation signals comprising:
        a coil,
        a tunable tank circuit configured to drive said coil at a frequency of resonance, and
        an adjusting circuit configured to control said frequency of resonance based on a feedback signal;
    an implantable stimulator including:
        a receiver configured to receive said stimulation signals,
        an electrode configured to apply said received stimulation signals to an aural nerve,
        a sensor configured to sense a parameter associated with said stimulation signals, and
        a monitor configured to generate said feedback signal in response to said sensed parameter.

2. The system of claim 1,
    wherein said transmitter is further configured to generate RF signals each having an amplitude, frequency and duty-cycle, and
    wherein said cochlear implant system further comprises a power controller configured to adjust said RF signals by changing at least one of said frequency, amplitude and duty cycle, based on said feedback signal.

3. The system of claim 1,
    wherein said sensor is further configured to sense an amplitude of said stimulation signals, and
    wherein said monitor is further configured to generate said feedback signal based on a range of said amplitude.

4. The system of claim 1,
    wherein said stimulator further comprises:
        an encoder configured to encode said parameter to generate an encoded signal capable of being transmitted to said processor, and
    wherein said processor further comprises:
        a decoder configured to decode said encoded parameter.

5. The system of claim 4,
    wherein said transmitter and said receiver are adapted to be inductively coupled, and
    wherein said encoded signal is adapted to be transmitted through said inductive coupling.

6. The system of claim 1, wherein said monitor comprises:
    a compliance monitor configured to determine when said stimulation signals are compliant.

7. The system of claim 6, further comprising:
    a controller configured to determine a ratio of compliant stimulation signals to a total number of stimulation signals.

8. The system of claim 7, wherein said controller is configured to adjust said power level to maintain said ratio at a predetermined target.

9. The system of claim 6, wherein said compliance monitor is further configured to generate said feedback signal when said stimulation signals are not compliant.

10. The system of claim 9, wherein said processor comprises:
    a power controller adapted to change said variable power level for a predetermined time period following said feedback signal.

11. The system of claim 9, wherein said processor comprises:
    a power controller adapted to change said variable power based on a ratio defined by a total number of stimulation signals and number of feedback signals related to said stimulation signals.

12. A cochlear implant system comprising:
    a processor configured to convert ambient sounds into stimulation signals;
    a transmitter configured to transmit said stimulation signals, and including;
        a tank circuit having a frequency of resonance, and
        an adjusting circuit arranged to control said frequency of resonance in response to a feedback signal; and
    an implantable stimulator including;
        a receiver configured to receive said stimulation signals,
        an electrode configured to apply said stimulation signals to an aural nerve,
        an energy storage element configured to store energy from said stimulation signals and provide power to said stimulator, and
        a power monitor configured to monitor a power parameter associated with said energy storage element and generating said feedback signal indicative of said parameter.

13. The system of claim 12, wherein said stimulator further comprises:
    an encoder configured to generate an encoded signal representing said power parameter, wherein said encoded signal is adapted to be transmitted to said processor, and wherein said processor includes a decoder configured to decode said encoded parameter.

14. The system of claim 13, wherein said transmitter and said receiver are adapted to be inductively coupled such that said encoded signal is can be transmitted through said inductive coupling.

15. A cochlear implant device comprising:
an external component comprising:
   a speech processor to generate encoded signals representing received ambient sound,
   an external coil,
   a tunable tank circuit to drive an external coil at resonant frequency, and
   an adjusting circuit to control said frequency of resonance in response to a feedback signal; and
an implantable component comprising:
   an internal coil configured to be inductively coupled to said external coil,
   a receiver configured to generate stimulation signals in response to said encoded signals received via said internal coil,
   at least one electrode configured to apply said stimulation signals to an auditory nerve,
   at least one condition monitor configured to generate said feedback signal indicative of a value of a monitored parameter in said implantable component.

16. The device of claim 15, wherein said internal component further comprises an internal power supply, and further wherein said feedback signal is indicative of an output of said internal power supply.

17. The device of claim 15, wherein said monitor comprises:
   a compliance monitor configured to monitor said stimulation signals as they are applied to said aural nerve and to generate a feedback signal indicative of a compliance condition of said stimulation signal.

18. The device of claim 17, wherein said external component adjusts said frequency of resonance based on a single feedback signal.

19. The device of claim 17, wherein said external component adjusts said frequency of resonance based on a ratio of compliant stimulation signals to a total number of stimulation signals.

* * * * *